US007862551B2

(12) United States Patent
Bates

(10) Patent No.: US 7,862,551 B2
(45) Date of Patent: Jan. 4, 2011

(54) APPARATUS AND METHODS FOR TREATING TISSUE USING PASSIVE INJECTION SYSTEMS

(75) Inventor: Mark C. Bates, Charleston, WV (US)

(73) Assignee: Nexeon MedSystems, Inc., Charleston, WV (US)

( * ) Notice: Subject to any disclaimer, the term of this patent is extended or adjusted under 35 U.S.C. 154(b) by 29 days.

(21) Appl. No.: 12/041,561

(22) Filed: Mar. 3, 2008

(65) Prior Publication Data

US 2008/0154201 A1  Jun. 26, 2008

Related U.S. Application Data

(63) Continuation of application No. 10/977,594, filed on Oct. 29, 2004, now Pat. No. 7,338,471, which is a continuation-in-part of application No. 10/894,810, filed on Jul. 19, 2004, now Pat. No. 7,632,262.

(51) Int. Cl.
*A61M 31/00* (2006.01)
(52) U.S. Cl. ...................................................... 604/506
(58) Field of Classification Search ............... 604/506, 604/511, 272, 273, 125, 187, 198, 264, 181, 604/131, 48, 57, 59–64, 110, 136, 137, 151, 604/152, 500, 507; 600/3, 7
See application file for complete search history.

(56) References Cited

U.S. PATENT DOCUMENTS

| 3,880,163 | A |   | 4/1975  | Ritterskamp |         |
|-----------|---|---|---------|-------------|---------|
| 4,067,334 | A |   | 1/1978  | Haller      |         |
| 4,108,177 | A | * | 8/1978  | Pistor      | 604/155 |
| 4,676,781 | A | * | 6/1987  | Phillips et al. | 604/135 |
| 4,710,162 | A | * | 12/1987 | Johnson     | 604/506 |
| 4,950,233 | A | * | 8/1990  | Abramowitz  | 604/512 |
| 5,244,460 | A |   | 9/1993  | Unger et al. |        |
| 5,273,532 | A | * | 12/1993 | Niezink et al. | 604/62 |
| 5,419,777 | A |   | 5/1995  | Hofling     |         |
| 5,531,780 | A | * | 7/1996  | Vachon      | 607/120 |
| 5,655,548 | A |   | 8/1997  | Nelson et al. |       |
| 5,730,741 | A |   | 3/1998  | Horzewski et al. |    |

(Continued)

FOREIGN PATENT DOCUMENTS

DE   299 03 726 U 1   7/1999

(Continued)

OTHER PUBLICATIONS

PCT International Search Report for PCT/US05/25469, 3 pages (mailed Oct. 3, 2006).

(Continued)

*Primary Examiner*—Theodore J Stigell
(74) *Attorney, Agent, or Firm*—Jones Day; Nicola A. Pisano

(57) ABSTRACT

Methods and apparatus are provided for treating damaged tissue using apparatus that atraumatically delivers a bioactive agent within the tissue, wherein the apparatus provides a column of stem cells may be advanced simultaneously with a needle during needle insertion, and then held stationary or injected at low pressure while retracting the needle. Alternatively, the needle may employ electromotive forces, or to change a dimension of the needle, to expel the bioactive agent into the needle track.

8 Claims, 6 Drawing Sheets

U.S. PATENT DOCUMENTS

| | | | |
|---|---|---|---|
| 5,860,739 A * | 1/1999 | Cannon | 366/177.1 |
| 5,910,150 A | 6/1999 | Saadat | |
| 5,941,893 A | 8/1999 | Saadat | |
| 6,024,120 A | 2/2000 | Yam et al. | |
| 6,051,008 A | 4/2000 | Saadat et al. | |
| 6,102,887 A | 8/2000 | Altman | |
| 6,120,520 A | 9/2000 | Saadat et al. | |
| 6,159,196 A | 12/2000 | Ruiz | |
| 6,264,637 B1 | 7/2001 | Hogan | |
| 6,302,870 B1 | 10/2001 | Jacobsen et al. | |
| 6,346,099 B1 | 2/2002 | Altman | |
| 6,432,119 B1 | 8/2002 | Saadat | |
| 6,544,236 B1 * | 4/2003 | Cragg et al. | 604/254 |
| 7,316,692 B2 | 1/2008 | Huffmaster | |
| 7,338,471 B2 | 3/2008 | Bates | |
| 2002/0049414 A1 | 4/2002 | Nobles | |
| 2003/0191449 A1 | 10/2003 | Nash et al. | |
| 2004/0092892 A1 * | 5/2004 | Kagan et al. | 604/264 |
| 2005/0124999 A1 * | 6/2005 | Teitelbaum et al. | 606/99 |
| 2005/0256361 A1 * | 11/2005 | Mathieu et al. | 600/7 |
| 2005/0261633 A1 | 11/2005 | Khalaj | |

FOREIGN PATENT DOCUMENTS

| | | |
|---|---|---|
| WO | WO 95/26776 | 10/1995 |

OTHER PUBLICATIONS

PCT International Search Report for PCT/US05/25470, 2 pages (mailed Sep. 21, 2006).

USPTO Office Action (non-final) for U.S. Appl. No. 10/977,594, 6 pages (mailed Dec. 15, 2006).

USPTO Notice of Allowance and Notice of Allowability for U.S. Appl. No. 10/977,594, 7 pages (mailed Oct. 9, 2007).

USPTO Office Action (non-final) for U.S. Appl. No. 10/894,810, 6 pages (mailed Jan. 17, 2007).

USPTO Office Action (final) for U.S. Appl. No. 10/894,810, 8 pages (mailed Aug. 28, 2007).

USPTO Office Action (non-final) for U.S. Appl. No. 10/894,810, 9 pages (mailed Jul. 25, 2008).

Bonan, "Local Drug Delivery for the Treatment of Thrombus and Restenosis," J. Invasive Cardiol., 8 (8): 399-402 (Oct. 1996).

Mack et al., "Biologic bypass with the use of adenovirus-mediated gene transfer of the complementary deoxyribonucleic acid for vascular endothelial growth factor 121 improves myocardial perfusion and function in the ischemic porcine heart," J. Thoracic and Cardiovascular Surgery 115 (1): 168-177 (1997).

Sanborn et al., "Percutaneous Endocardial Gene Therapy: In Vivo Gene Transfer and Expression" (abstract), J. Am. Coll. Card. 33 (2 Suppl.): 262A (Feb. 1999).

Thompson et al., "Percutaneous Transvenous Cellular Cardiomyoplasty," J. Am. Coll. Card. 41 (11) 1964-1971 (Jun. 2003).

Uchida et al., "Angiogenic therapy of acute myocardial infarction by basic fibroblast growth factor and heparin sulfate," American Heart Journal 130 (6): 1182-1188 (Dec. 1995).

USPTO Notice of Allowance for U.S. Appl. No. 10/894,810, mailed Aug. 6, 2009 (6 pages).

USPTO Final Office Action for U.S. Appl. No. 10/894,810. mailed Feb. 24, 2009 (8 pages).

* cited by examiner

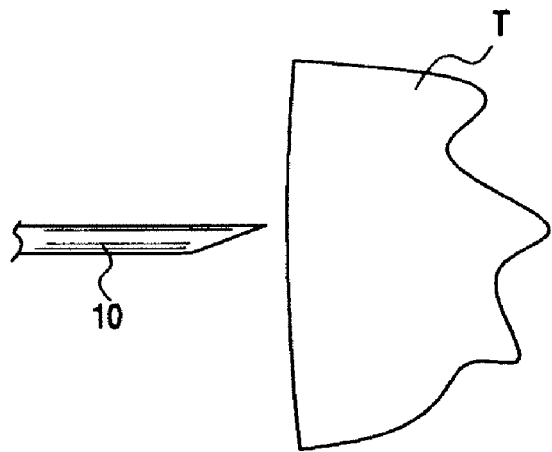
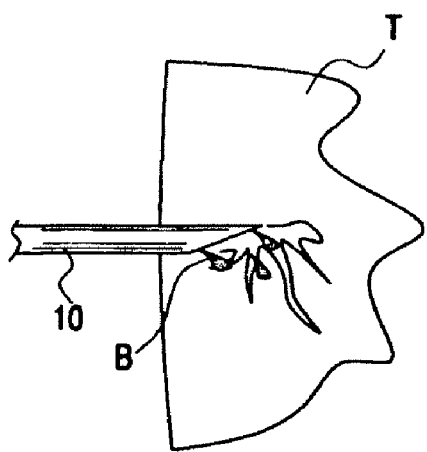
FIG.1A
(PRIOR ART)
FIG.1B
(PRIOR ART)
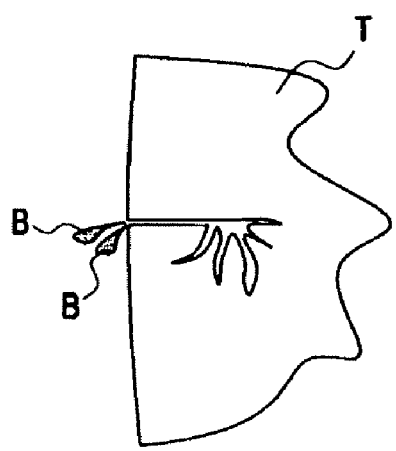
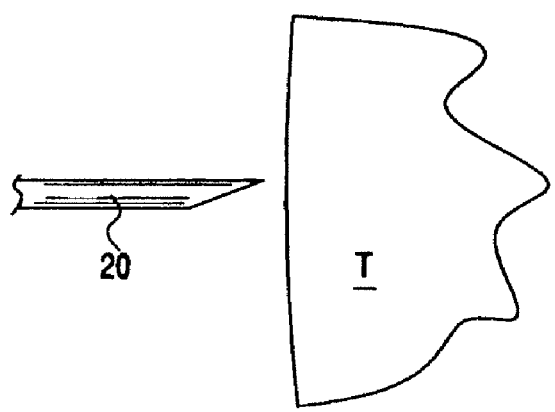
FIG.1C
(PRIOR ART)
FIG.2A

APPARATUS AND METHODS FOR TREATING TISSUE USING PASSIVE INJECTION SYSTEMS

REFERENCE TO RELATED APPLICATIONS

This application is a continuation of U.S. patent application Ser. No. 10/977,594, filed Oct. 29, 2004, now U.S. Pat. No. 7,338,471, issued on Mar. 4, 2008, the entire contents of which are incorporated herein by reference, which is a continuation-in-part of U.S. patent application Ser. No. 10/894,810, filed Jul. 19, 2004, now U.S. Pat. No. 7,632,262, issued on Dec. 15, 2009, the entire contents of which are incorporated herein by reference.

FIELD OF THE INVENTION

The present invention relates to apparatus and method for treating an injured spinal cord and other injured tissue using passive injection systems that reduce barotrauma to the injected material and collateral damage to the host tissue.

BACKGROUND OF THE INVENTION

Spinal cord injuries may arise from car accidents, violent crimes, falls and sports injuries. Spinal cord injury is a major neurological problem since most damage resulting from the injury is irreversible. Injured nerves fibers do not normally regenerate with resulting loss of nerve cell communication, leading to paralysis and loss of sensation.

After spinal cord severance, a new glial basal lamina forms to cover the exposed surface of the cord end regions. The glial cells also secrete barrier molecules that are difficult to penetrate, further suppressing reestablishment of nerve interconnections. The spinal cord tissue bordering the severed region becomes necrotic, detaches from the spinal cord, and develops irregular cavities.

Most tissue in the human body originates from undifferentiated cells known as stem cells. These fundamental building blocks differentiate into specific target parenchymal tissue based on hormonal and other local signals. Scientific evidence suggests that stem cells injected into a target tissue will differentiate into a cell line specific to the host tissue. This capability is of particular interest in treating conditions involving organs, such as the spinal cord, heart and brain that cannot regenerate.

Initial enthusiasm concerning stem cell implantation in patients was tempered by the ethical and logistic concerns of utilizing embryonic stem cells. Recent developments in stem cell research suggest adult stem cells can be harvested from the bone marrow and other tissues. Many such "cell lines" have been generated and are undergoing clinical evaluation. If successful, this work will obviate the moral and ethical dilemma of utilizing tissue from embryos for research.

Pressurized direct injection of certain bioactive agents, such as stem cells, is expected to inflict physical damage to the cell membranes due to fluid turbulence and pressure fluctuations (referred to herein as "barotrauma") during the injection process. The damage may include lysis of the cells or injury to the cells that may significantly reduce the yield of viable cells delivered at the injection site and/or trauma to the target tissue. Forceful injection of any material into tissue also may disrupt the delicate intercellular matrix, thereby causing target tissue cellular injury.

In view of these drawbacks of previously known apparatus and methods, it would be desirable to provide methods and apparatus for treating severed or injured spinal cords by atraumatically delivering a bioactive agent, e.g., stem cells, within or adjacent to the injured spinal cord to promote nerve regeneration.

It would be also desirable to provide methods and apparatus for treating spinal cord injury by is delivering a bioactive agent so as to reduce the risk of barotrauma to the agent and target tissue during delivery.

It would be further desirable to provide apparatus and methods for treating spinal cord injury by delivering a bioactive agent to damaged tissue to promote tissue regeneration, wherein the apparatus and methods enhance the proportion of viable material delivered to the damaged tissue.

It further would be desirable to provide apparatus and methods for treating a spinal cord injury to cause nerve regeneration of both the sensory and motor nerves in the spinal cord.

SUMMARY OF THE INVENTION

In view of the foregoing, it is an object of the present invention to provide methods and apparatus for treating spinal cord injury or other nerve or muscle tissue by atraumatically delivering a bioactive agent within or adjacent to an injured portion of the nerve or muscle to promote regeneration.

It is another object of this invention to provide methods and apparatus for treating spinal cord injury by delivering a bioactive agent so as to reduce the risk of barotrauma to the agent and target tissue during delivery.

It also is an object of this invention to provide apparatus and methods for treating spinal cord injury by delivering a bioactive agent to damaged tissue to promote tissue regeneration, wherein the apparatus and methods enhance the proportion of viable material delivered to the damaged tissue.

It is a further object of the present invention to provide apparatus and methods for treating spinal cord injury to cause nerve regeneration of both the sensory and motor nerves in the spinal cord.

These and other objects of the present invention are accomplished by providing methods and apparatus for delivering bioactive agents, preferably including stem cells or other precursor cells, to treat spinal cord injury, wherein the stem cells are delivered atraumatically. In the context of the present invention, "atraumatic" deployment means deployment of the stem cells without generating turbulent fluid motion that inflicts physical damage to the stem cells, e.g., due to high shearing stresses or pressure fluctuations. The bioactive agent preferably is delivered in a solution comprising nutrients to foster stem cell survival after implantation, and one or more drugs or hormones to suppress inflammatory response, etc.

In accordance with the principles of the present invention, the bioactive agent is directly deployed in a needle track formed in a target tissue mass following formation of the needle track. In this manner, the bioactive agent is not subject to barotrauma during delivery, nor does forceful impingement of the injectate during delivery disrupt the pre-existing intercellular matrix.

Deployment of stem cells preferably is accomplished using needle arrangements that avoid impingement of the stem cells against target tissue at high velocity by employing low-pressure injection, capillary action or electrostatic forces to eject the stem cells out of the needle during needle withdrawal. In one preferred embodiment, a column of stem cells may be advanced simultaneously with a needle during needle insertion, and then held stationary while retracting the needle. In another embodiment the needle comprises an electroactive polymer that contracts along its length to expel the stem cells into the needle track. In a further embodiment, electromotive forces are employed to deposit the stem cells into the needle track. According to some embodiments, a grid may be positioned over the injured portion of the spinal cord to guide injections of the bioactive agent.

While the present invention is described in the context of promoting regeneration of spinal cord tissue, the apparatus and methods of the present invention advantageously may be employed wherever it is desired to promote tissue regeneration, such as in the heart, kidney, liver, brain and other organs and muscles.

Methods of using the apparatus of the present invention also are provided.

BRIEF DESCRIPTION OF THE DRAWINGS

Further features of the invention, its nature and various advantages will be more apparent from the accompanying drawings and the following detailed description of the preferred embodiments, in which:

FIGS. 1A-1C are views depicting previously known methods of injecting drugs and other bioactive agents into a tissue mass;

FIGS. 2A-2C are views depicting a method of injecting drugs and other bioactive agents into a tissue mass in accordance with the principles of the present invention;

DETAILED DESCRIPTION OF THE INVENTION

Referring to FIGS. 1A-1C, some of the drawbacks of previously known bioactive agent delivery systems are described. FIG. 1A illustrates a previously known injection needle 10 being brought into approximation with tissue mass T. Once the tip of needle 10 is inserted into the tissue, as shown in FIG. 1B, bioactive agent B, which may comprise stem cells, is injected into the tissue mass.

Applicant has discovered that pressurized injection of a bioactive agent may have a substantial detrimental effect both on the agent delivered and the tissue to be treated. For example, applicant has conducted studies in which it had been observed that pressurized injection causes the injectate stream to impinge violently against the tissue as it leaves the tip of the injection needle. During injection, the injectate stream is turbulent, and may experience rapid localized pressure fluctuations. These effects may damage the bioactive agent, particularly where the agent comprises stem cells, by rupturing the cell membrane or injuring the cellular components.

In addition, as illustrated in FIG. 1C, once needle 10 has been withdrawn from the needle track N, the potential exists for the injected bioactive agent B to be expelled from the needle track, with concomitant risk of embolization. Applicant has concluded that a higher yield of viable cells may be delivered to a target tissue if apparatus and methods could be provided that reduce the effects of pressurized injection, including lysis and expulsion.

Figure 2B:
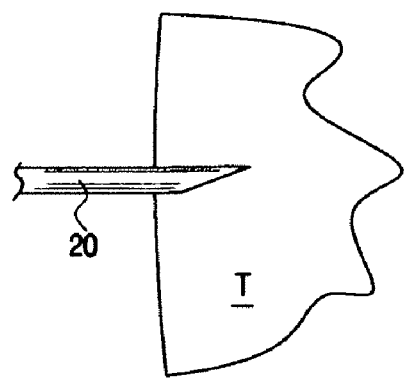
Figure 2C:
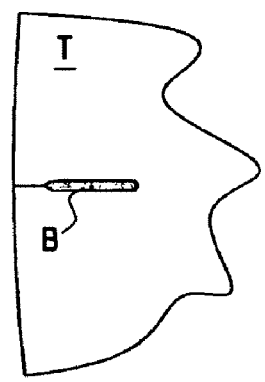

Referring now to FIGS. 2A to 2C, apparatus and methods of the present invention are described that overcome the drawbacks of previously known systems for delivering fragile bioactive agents, such as stem cells. As shown in FIG. 2A, in accordance with the principles of the present invention, needle 20 is first approximated to spinal cord tissue mass T. In FIG. 2B, needle 20 is shown inserted into the tissue mass. In FIG. 2C, as needle 20 is withdrawn from the tissue mass, bioactive agent B is delivered from the tip of the needle and deposited in the needle track.

In accordance with the principles of the present invention, the bioactive agent is injected into the tissue under little pressure and with substantially less turbulence and localized pressure fluctuation than in previously known injection systems. Also, the bioactive agent will not damage the tissue mass by splitting the tissue along naturally-occurring striations. These benefits of atraumatic injection may be particularly advantageous in the repair of an injured or severed spinal cord.

Figure 3A:
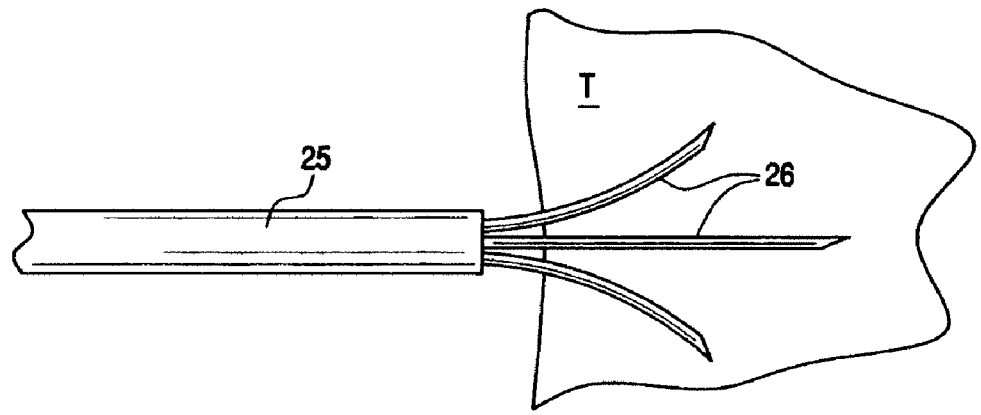
FIGS. 3A and 3B are views depicting apparatus of the present invention for injecting drugs and other bioactive agents into a tissue mass at multiple sites simultaneously.
Figure 3B:
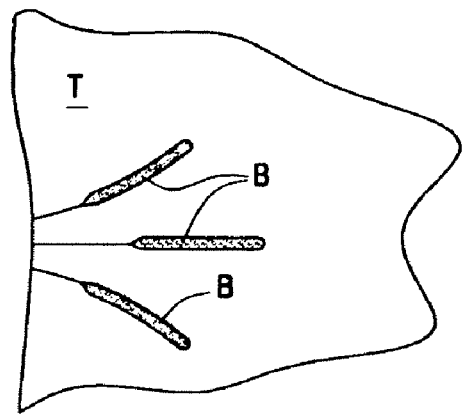

In FIGS. 3A and 3B, apparatus constructed in accordance with the principles of the present invention is described, in which distal end 25 includes selectively extendable needles 26. As depicted in the Figures, needles 26 are configured to flare outward when extended beyond distal end 25 of the apparatus, thereby enhancing dispersal of the bioactive agent into tissue mass T. As described above for the embodiment of FIG. 2, needles 26 are configured to delivery bioactive agent B into the tissue mass while minimizing barotrauma to the bioactive agent and the injury to the tissue mass. Although distal end 25 illustratively includes three needles 26, a greater or lesser number of needles may be employed without departing from the spirit of the present invention.

Figure 4A:
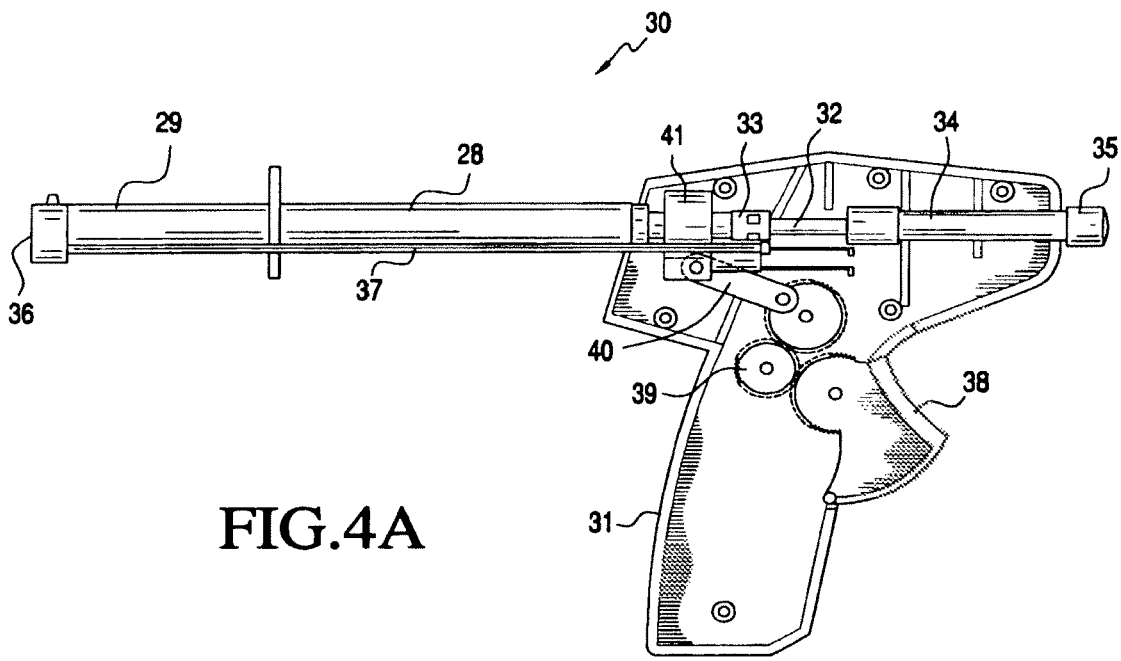
FIGS. 4A and 4B are, respectively, a side view, partly in section, and isolation view of the internal components of apparatus of the present invention.
Figure 4B:
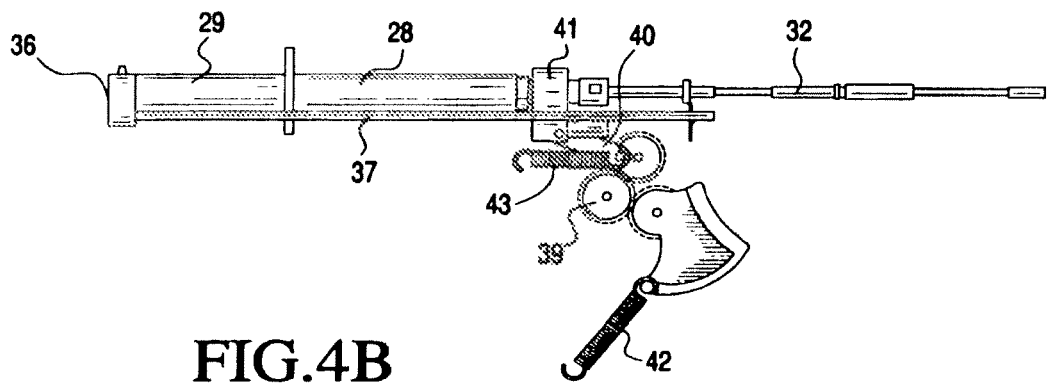

Referring now to FIGS. 4A and 4B, apparatus constructed in accordance with the principles of the present invention is described. Apparatus 30 comprises handle 31 that is configured to accept conventional syringe 28, which may be loaded with a preselected bioactive agent, such as stem cells in a nutrient solution. The barrel of syringe 28 is removably coupled to tube 32 via fluid-tight seal 33. Tube 32, which carries one or more tissue-piercing needles at its distal end, is arranged to reciprocate through sleeve 34 so that the distal tip of the needle extends beyond bushing 35 when the device is actuated. Piston 29 of syringe 28 is removably coupled to block 36 and rails 37.

Handle 31 includes trigger 38 that may be depressed to selectively actuate apparatus 30. In particular, trigger 38 is coupled to tube 32 via gear train 39 and linkage 40. Clamp 41 is configured to grip and reciprocate the body of the syringe in accordance with the degree of actuation of trigger 38. Each of rails 37 preferably includes a portion that forms a rack to permit forward movement of piston 29 of the syringe during a first range of motion of trigger 38, and then retain piston 29 stationary relative to rails 37 during a second range of motion of the trigger.

Link 40 is coupled to clamp 41 so that, after syringe 28 and piston 29 are advanced during the initial range of motion of the trigger, the piston is held stationary while clamp 41 retracts tube 32 and needles from the needle track(s) and simultaneously urges the body of syringe 28 proximally. This motion causes the bioactive material within syringe 28 to be dispensed into the needle track(s) (see FIGS. 2 and 3) at low velocity and with little or no barotrauma. As depicted in FIG. 4B (but omitted elsewhere for clarity), trigger 38 and link 40 preferably are biased by springs 42 and 43, respectively, to return the mechanism to its starting position when trigger 38 is released.

Figure 5A:
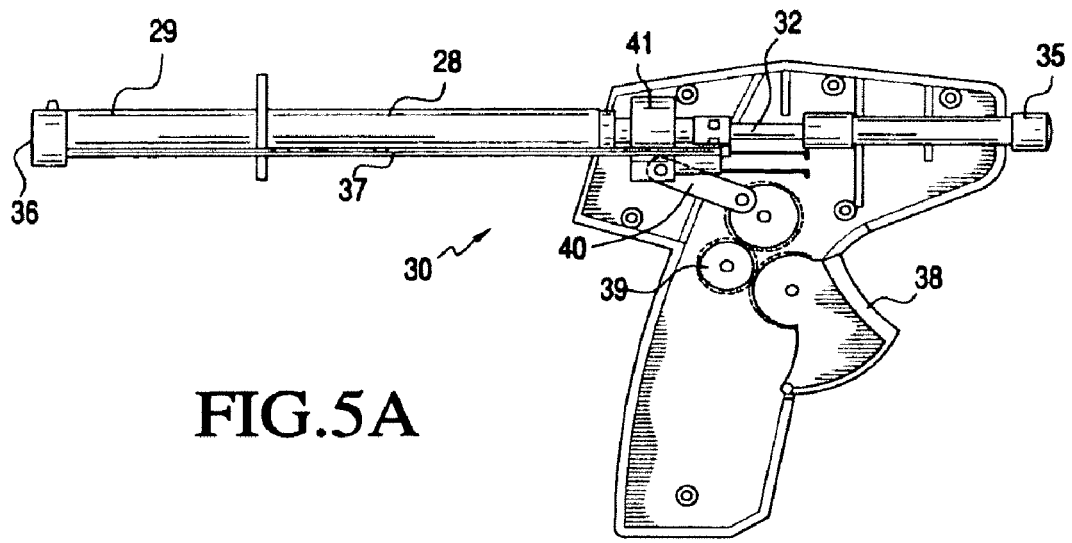
FIGS. 5A-5C depict operation of the apparatus of FIG. 4.
Figure 5B:
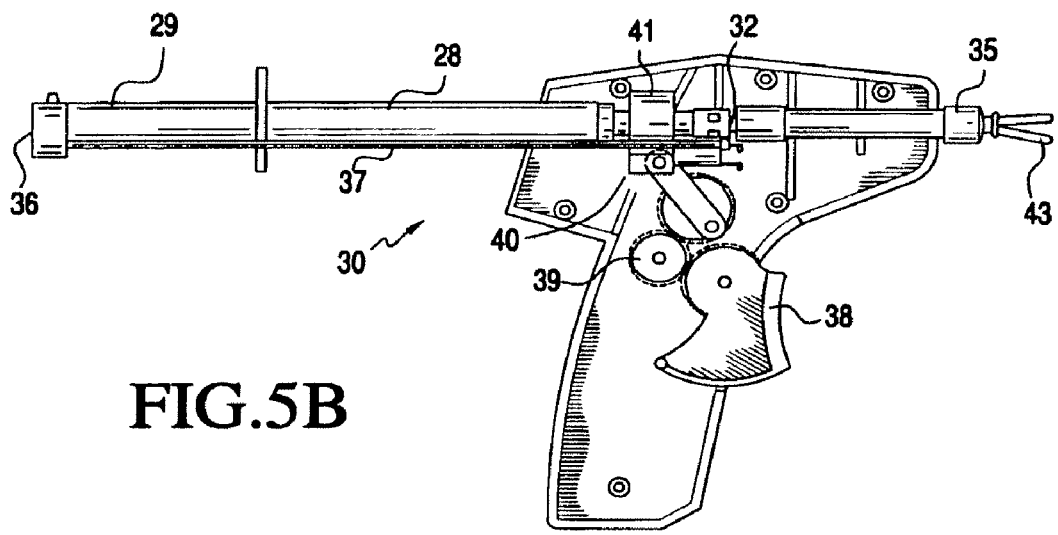
Figure 5C:
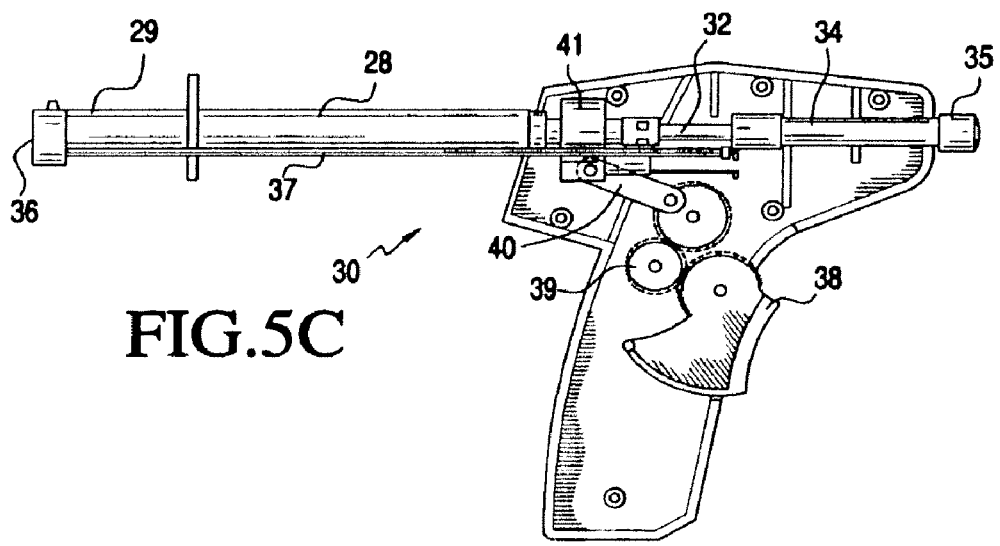

Referring now also to FIGS. 5A-5C, operation of apparatus 30 is described. In FIG. 5A, trigger 38 of the apparatus is shown at its initial position, and with syringe 28 and piston 29 in the proximal-most positions. As shown in FIG. 5B, as the trigger 38 is depressed about half-way through its range of motion, gear train 39 and link 40 urge syringe 28, piston 29 and rails 37 in the distal direction in unison. This in turn causes tube 32 and clamp 41 to be advanced distally, in turn causing needles 43 to extend beyond bushing 35. Illustratively, the tissue-piercing end of tube 33 includes three needles 43 that flare outward upon entering into a tissue mass, as depicted in FIG. 3A. Because syringe 28 and piston 29 are moved in unison, the bioactive agent contained within syringe 28 is subjected to substantially no hydraulic forces, and the distance between block 36 and the proximal-most portion of syringe 28 remains unchanged.

As further depicted in FIG. 5C, continued depression of trigger 38 causes link 40 to begin retracting tube 32 in the proximal direction. This motion also drives clamp 41 in the proximal direction. Because the rack portions of rails 37 disengage from link 40 and gear train 39 during proximal movement of clamp 41, rails 37 and piston 29 remain stationary. Consequently, proximal movement of clamp 41 and tube 32 both retracts needles 43 from the needle tracks formed in the tissue, and urges the body of syringe 28 against piston 29.

Still referring to FIG. 5C, proximal translation of clamp 41 also causes the distance between block 36 and the proximal-most portion of syringe 28 to shorten. This action applies sufficient pressure to the contents of syringe 28 to dispense the bioactive agent into the needle tracks formed by needles 43 as the needles withdraw from the tissue. When the clinician releases trigger 38, springs 42 and 43 return tube 32 and clamp 41 to the starting position, shown in FIG. 5A. Apparatus 30 then may be repositioned, and the above process repeated.

As will be appreciated, the volume of injected material delivered into the target tissue may be adjusted depending upon the target tissue milieu. For example, for tissue or muscle that is fairly elastic, such as heart muscle, additional material may be injected to create low-pressure compartments within the tissue. On the other hand, lower volumes may be employed in less resilient structures, such as the spinal cord and brain.

Figure 6A:
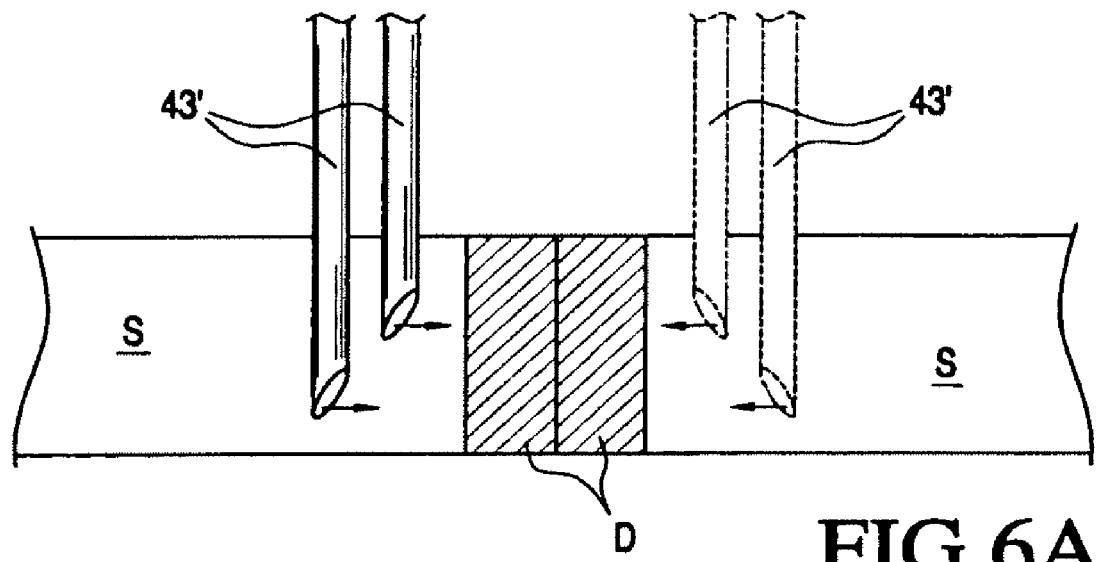
FIGS. 6A and 6B are cross-sectional views of apparatus and methods of the present invention for injecting a bioactive agent into an injured spinal cord.
Figure 6B:
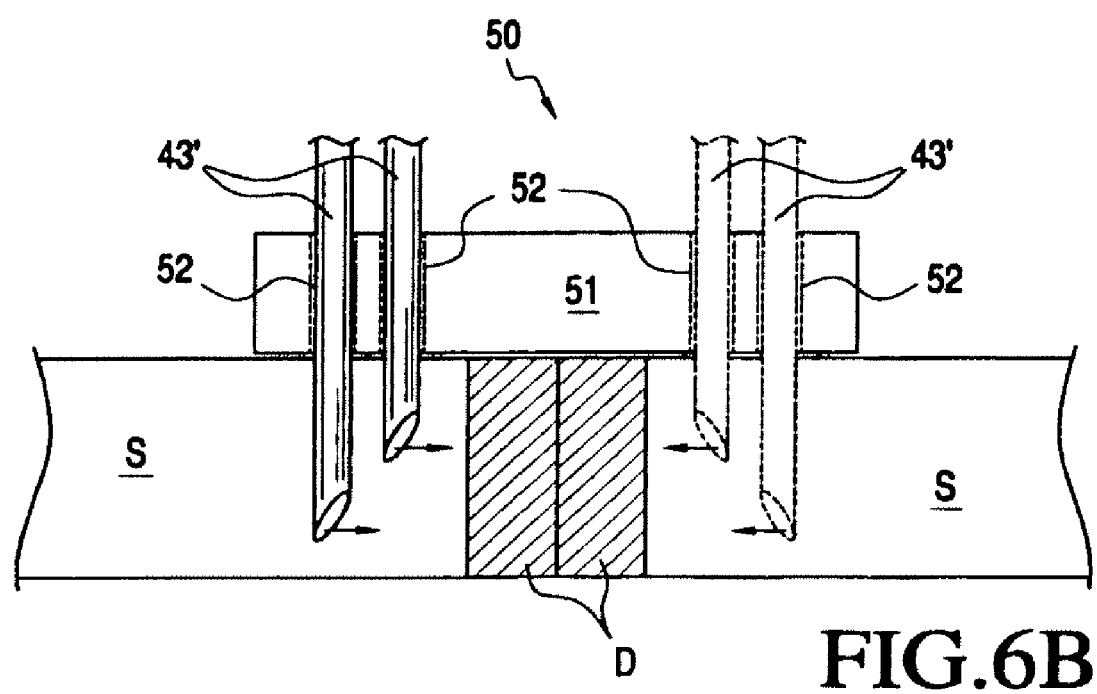

With respect to FIGS. 6A and 6B, in accordance with another aspect of the invention, needles 43' of apparatus 30 may have different predetermined lengths so as to deliver the bioactive agent at various depths within spinal cord S to treat injured region D. As illustrated in FIG. 6A, needles 43' may first be used to deliver bioactive agent on a first side of a severed region D of spinal cord S, and then moved and applied to the opposite side of the severed region (shown in dotted line in FIG. 6A). Additionally, needles 43' may be arranged to be individually rotated so that the bioactive agent is dispersed in preselected directions.

FIG. 6B depicts the use of grid 50 to guide needles 43' into predetermined locations along spinal cord S. Grid 50 comprises block 51 having a plurality of through holes 52 disposed along its surface to provide a predetermined separation between injection regions. Advantageously, grid 50 lends structural support to damaged spinal region D during stem cell injection. As in the method depicted in FIG. 6A, apparatus 30 may be used to inject needles 43' at a first location, and then repositioned using grid 50 (as shown in dotted line) to provide subsequent injections.

With further reference to FIG. 6, according to some methods of the present invention, a predetermined amount of cerebrospinal fluid may be removed from spinal cord S prior to injecting the bioactive agent. Preferably, the amount of cerebrospinal fluid removed is substantially equivalent to the amount of bioactive agent, e.g., stem cell solution, injected into the spinal cord. This step of the method is expected to enhance atraumatic delivery of the bioactive agent by reducing the risk that the injection prevents injury to the spinal artery or surrounding delicate tissue during injection.

Figures 7A, 7B:
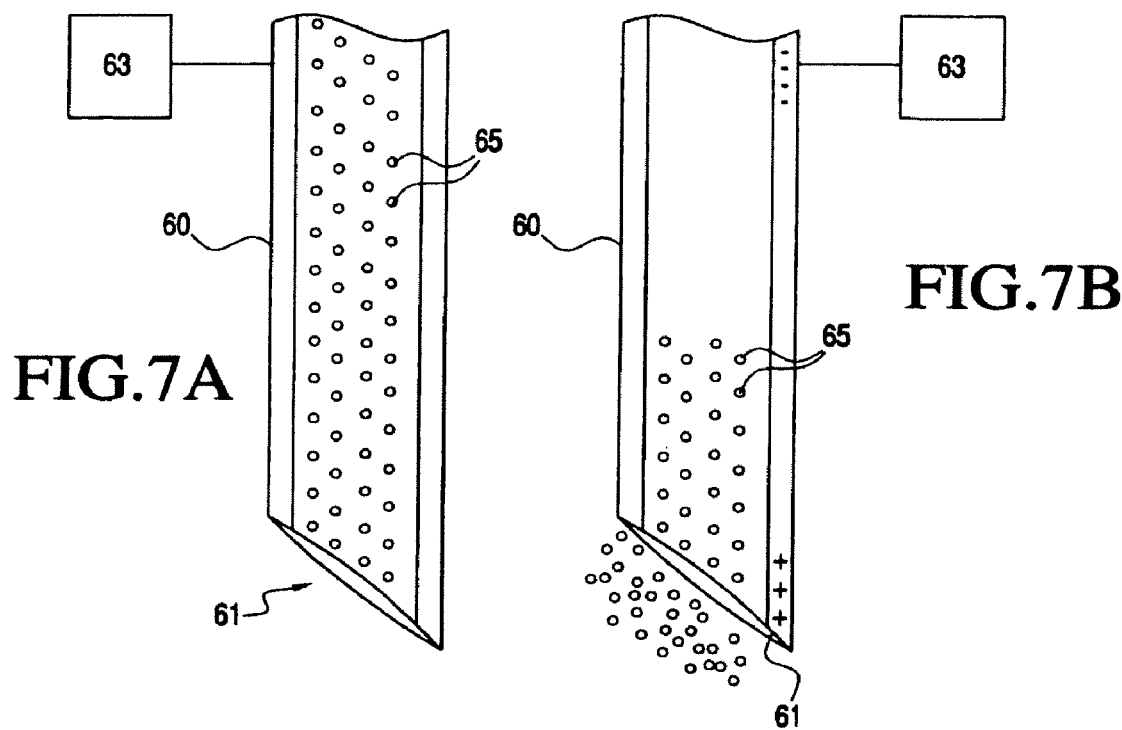
FIGS. 7A and 7B are cross-sectional views of another embodiment of the apparatus of the present invention.

Referring now to FIGS. 7A and 7B, an alternative embodiment of an injection needle constructed in accordance with the principles of the present invention is described. Needle 60 comprises a glass or polymer microfiber adapted to receive and transmit electric signals, and includes tissue-piercing distal end 61 and interior lumen 62. Needle 60 is loaded with a bioactive agent, preferably comprising stem cells 65, and in addition is coupled to power supply 63 that applies an electric field longitudinally along needle 60.

When energized by power supply 63, an electric field is applied to needle 60 that attracts negatively charged stem cells 65 toward end 61, where they are deposited into the spinal cord. In particular, as depicted in FIG. 7B, a positive charge is induced at distal end 61 of needle 60, thereby causing negatively charged stem cells 65 to be drawn to the distal tip of the needle.

Stem cells 95 are believed to be negatively charged in the natural state, so that they are drawn toward the positive charge at distal end 61 of needle 60. Alternatively, an ionic solution containing negatively charged particles may be added to the bioactive agent prior to injection to increase the attraction of the stem cells towards a positive charge. The movement of stem cells 65 toward the positive charge causes a predetermined amount of the stem cells to be ejected from distal end 61 into a target tissue mass, such as a damaged region of spinal cord. Needle 60 optionally may transmit a signal that defines a location of the needle when viewed using an MRI or CT device.

Figures 8A, 8B:
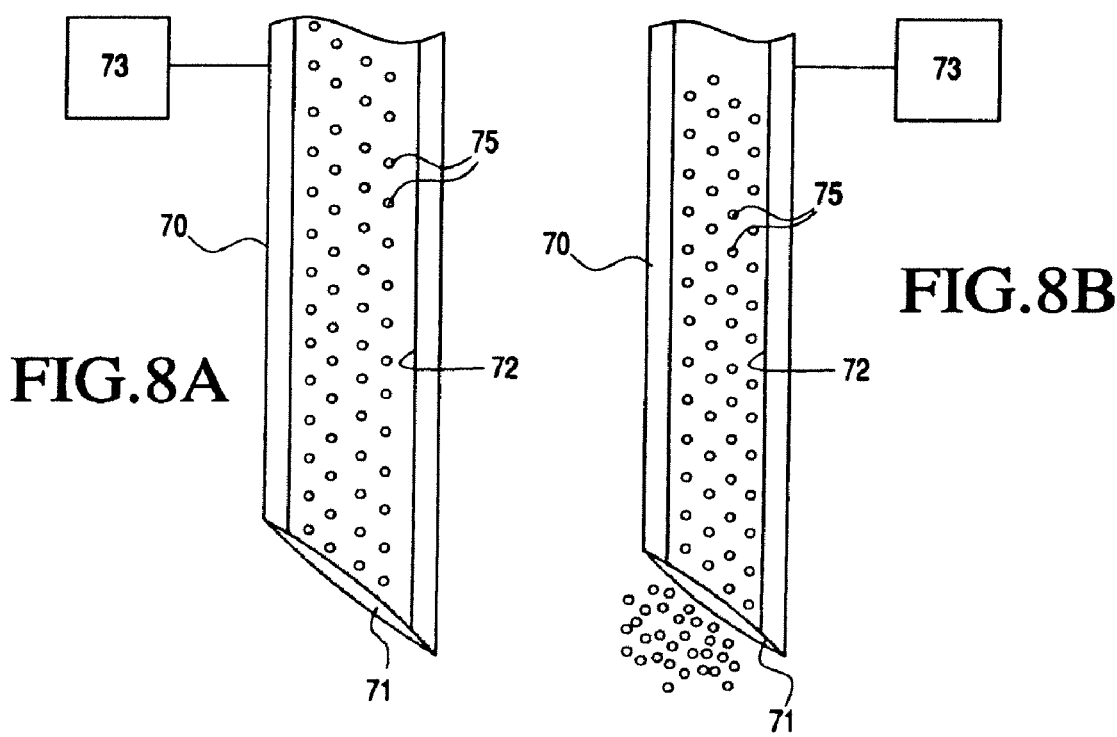
FIGS. 8A and 8B are cross-sectional views of a further alternative embodiment of apparatus of the present invention.

Referring now to FIGS. 8A and 8B, another alternative embodiment of the present invention is described. Needle 70 comprises an electroactive polymer that forms an actuator, and includes tissue-piercing distal end 71 and interior lumen 72. Needle 70 is loaded with a bioactive agent, preferably comprising stem cells 75, and is coupled to power supply 73 that applies an electric field longitudinally along needle 70. Electroactive polymers are members of the family of plastics referred to as "conducting polymers," and are preferred for the practice of the present invention due to their small size, large force and strain and low cost.

In FIG. 8, injection needle 70 comprises an electroactive polymer that is adapted to contract in response to electrical stimulation. Suitable electroactive polymers include, but are not limited to, polypyrrole, polyacetylene, polyaniline and polysulfone. Oxidation or reduction of these polymers leads to a charge imbalance that results in a flow of ions (dopants) into the material in order to balance charge. The ions enter the polymer from an tonically conductive electrolyte medium that is coupled to the polymer surface. Conversely, if ions are already present in the polymer when it is oxidized or reduced, they may exit the polymer.

Dimensional changes in electroactive polymers may be triggered by the mass transfer of ions into or out of the polymer. For some electroactive polymers, the expansion is due to ion insertion between chains, whereas repulsion between chains is the dominant effect for other electroactive polymers. The mass transfer of ions into and out of the electroactive polymer leads to an expansion or contraction of the polymer. In this manner, needle 70 may be contracted such that a predetermined amount of bioactive agent is ejected from distal end 71 of the needle.

More specifically, needle 70 comprises an electroactive polymer that is configured to contract when an electric charge is applied to the needle by power supply 73. Needle 70 has a first diameter (FIG. 8A) and a second, contracted diameter (FIG. 8B) when energized. Referring to FIG. 8B, when an electrostatic charge is applied to injection needle 70, the needle contracts and the diameter of lumen 72 decreases, thereby expelling a predetermined amount of stem cells 75 out of distal end 71 of needle 70. It is expected that constriction of lumen 72 is a bulk phenomenon that imposes a low-level distributed compressive force to the bioactive agent disposed in the lumen. Accordingly, substantially smaller local pressure fluctations will be imposed on the bioactive agent as compared to pressurized injection using a syringe, thereby reducing barotrauma and leading to substantially better viability of the implanted stem cells.

As will of course be understood, the embodiments of FIGS. 7 and 8 may include multiple needle tips to deliver bioactive agent at several sites or depths simultaneously, and may be used with a grid, such as described with respect to FIG. 6, to deliver the bioactive agent according to a predetermined pattern. As will further be understood, power supplies 63 and 73 of the embodiments of FIGS. 7 and 8, respectively, may include controllers that control operation of the electric fields applied to the needles so that predetermined amounts of bioactive agent are delivered by the needles when activated.

While preferred illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed is:

1. A method of atraumatically injecting a bioactive agent into tissue, the method comprising:

(a) providing a device having a syringe, an actuator with a trigger, and an injection needle, the syringe comprising a piston and a body containing the bioactive agent, the syringe and the injection needle coupled to the actuator and configured so that depression of the trigger in a first range of motion causes the injection needle, the body, and the piston to extend in a distal direction in unison, and continued depression of the trigger in a second range of motion causes the injection needle and the body to retract in a proximal direction in unison while the piston remains stationary, and wherein the body of the syringe reciprocates in accordance with a degree of actuation of the trigger;

(b) approximating the device to the tissue with the injection needle in a retracted status;

(c) depressing the trigger in the first range of motion to insert the injection needle into the tissue and form a needle track in the tissue; and (d) thereafter, further depressing the trigger in the second range of motion to withdraw the injection needle from the needle track while atraumatically delivering the bioactive agent into the needle track.

2. The method of claim 1, wherein the actuator comprises a clamp and a block, the method further comprising:

coupling the body of the syringe and the injection needle to the clamp; and coupling the piston of the syringe to the block;

wherein (c) comprises causing the clamp and the block to move in the distal direction, the clamp moving the body of the syringe and the injection needle in the distal direction, the block moving the piston in the distal direction; and wherein (d) comprises causing the clamp to move in the proximal direction and the block to remain stationary, the clamp moving the body of the syringe and the injection needle in the proximal direction, the block holding the piston stationary.

3. The method of claim 1, wherein the bioactive agent comprises stem cells.

4. The method of claim 1, wherein the tissue comprises one of spinal cord tissue, heart tissue, brain tissue, kidney tissue, or liver tissue.

5. The method of claim 1, wherein during (d) the bioactive agent is deposited in a predefined portion of the needle track.

6. The method of claim 5, wherein the predefined portion of the needle track comprises a distal portion of the needle track.

7. The method of claim 1, wherein the injection needle forms a curved needle track in the tissue.

8. The method of claim 1, further comprising positioning the injection needle into a tube, the tube being coupled to the body of the syringe.

* * * * *